US012721743B2

(12) United States Patent
Huang et al.

(10) Patent No.: US 12,721,743 B2
(45) Date of Patent: Sep. 1, 2026

(54) TOE CORRECTOR

(71) Applicant: Tao Wang, Dongguan (CN)

(72) Inventors: Qingyu Huang, Dongguan (CN); Weiping Qiu, Dongguan (CN)

(73) Assignee: Tao Wang, Dongguan (CN)

( * ) Notice: Subject to any disclaimer, the term of this patent is extended or adjusted under 35 U.S.C. 154(b) by 0 days.

(21) Appl. No.: 19/325,549

(22) Filed: Sep. 11, 2025

(65) Prior Publication Data

US 2026/0007534 A1 Jan. 8, 2026

(30) Foreign Application Priority Data

Dec. 10, 2024 (CN) ......................... 202423047968.8

(51) Int. Cl.
*A61F 5/01* (2006.01)

(52) U.S. Cl.
CPC ...... *A61F 5/019* (2013.01); *A61F 2005/0197* (2013.01)

(58) Field of Classification Search
CPC ...... A61F 5/019; A61F 5/0127; A61F 13/063; A61F 13/064; A61F 13/068; A61F 2005/0134; A61H 1/0266; A61H 2001/027
See application file for complete search history.

(56) References Cited

U.S. PATENT DOCUMENTS 7,473,234 B1 * 1/2009 Weltner .................. A61F 5/013 602/5
11,839,564 B1 * 12/2023 Solotoff ................ A61F 5/0125
2005/0187506 A1 * 8/2005 Reinhardt ............... A61F 5/019 602/30
2011/0130695 A1 6/2011 Rafique
2017/0273866 A1 9/2017 Jang
2019/0151133 A1 * 5/2019 Lee ......................... A61F 5/013
2022/0168127 A1 * 6/2022 Jiang ....................... A61F 5/012
2024/0315863 A1 9/2024 Tao
2025/0345199 A1 * 11/2025 Cai ......................... A61F 5/019

* cited by examiner

*Primary Examiner* — Kari K Rodriquez

(57) ABSTRACT

A toe corrector includes a fastening bracket extending longitudinally, correction bracket extending longitudinally, and rotational adjustment mechanism for adjusting the correction bracket. An adjustable fastening strap for fastening the fastening bracket to a medial side of a foot is disposed on the fastening bracket. An adjustable correction strap for fastening the correction bracket to the medial side of the foot is disposed on the correction bracket. The rotational adjustment mechanism includes an adjustment knob disposed on the fastening bracket and adjustment gear, where a drive gear coaxial with the adjustment knob is disposed at a lower end of the adjustment knob, and is in meshing engagement with the adjustment gear that is connected to the correction bracket, the adjustment knob and the adjustment gear are constructed to enable the fastening bracket to be in articulated joint with the correction bracket that is horizontally rotatable relative to the fastening bracket.

7 Claims, 6 Drawing Sheets

TOE CORRECTOR

TECHNICAL FIELD

The present disclosure belongs to the field of toe corrector technologies, and in particular, relates to a novel toe corrector.

BACKGROUND

Currently, factors such as improper footwear or ill-fitting shoes result in bunion, toe deformity, and the like, creating a need for orthotic devices to correct foot alignment. However, many orthotic devices currently on the market have non-adjustable angles, are cumbersome to use and operate, poor in correction effect, small in scope of application, and poor in versatility. For example, the South Korean patent with an application number of KR1020220011071 discloses a technical solution capable of achieving correction adjustment of the big toe relative to upward and downward rotation. However, its correction method has limitations. Therefore, a toe corrector capable of performing adjustment work is needed to resolve the technical problems.

SUMMARY

To resolve the above problems, the present disclosure provides the following technical solutions:

A novel toe corrector is provided, including: a fastening bracket that extends longitudinally, a correction bracket that extends longitudinally, and a rotational adjustment mechanism configured to adjust the correction bracket, where an adjustable fastening strap that is configured to fasten the fastening bracket to a medial side of a foot is disposed on the fastening bracket;

an adjustable correction strap that is configured to fasten the correction bracket to the medial side of the foot is disposed on the correction bracket; and the rotational adjustment mechanism includes an adjustment knob that is disposed on the fastening bracket and an adjustment gear, where a drive gear that is coaxial with the adjustment knob is disposed at a lower end of the adjustment knob, the drive gear is in meshing engagement with the adjustment gear, the adjustment gear is connected to the correction bracket, the adjustment knob and the adjustment gear are constructed to enable the fastening bracket to be in articulated joint with the correction bracket, and the correction bracket is horizontally rotatable relative to the fastening bracket.

Further, the rotational adjustment mechanism further includes a compound gear that is in meshing engagement between the adjustment knob and the adjustment gear, and two gear rings of the compound gear are respectively in meshing engagement with the drive gear and the adjustment gear.

Further, a gearbox housing configured to mount the rotational adjustment mechanism is disposed on the fastening bracket; and two articulated connection arms extending toward the correction bracket are respectively formed on two sides of the gearbox housing, a pivot shaft is disposed at an end of the correction bracket, the pivot shaft is received between the two articulated connection arms, and is in articulated joint with the two articulated connection arms, and the adjustment gear is disposed in the pivot shaft and is coaxial with the pivot shaft.

Further, the adjustment knob is axially movably engaged with the gearbox housing, and ratchets that are circumferentially disposed are formed on a lower end surface of the drive gear; and pawls that correspond to the ratchets are disposed at a bottom of the gearbox housing, and the ratchets are engaged with the pawls to form a ratchet mechanism.

Further, the adjustment knob is configured to be movable and pluggable in an axial direction in the gearbox housing; a central shaft extending downward is formed at a lower end of the adjustment knob; a mounting shaft hole for allowing the central shaft to insert is provided in the gearbox housing; and a limiting flange extending inward is formed on an upper edge of the mounting shaft hole; and a spring contact strip that is elastically connected to the central shaft is formed on the central shaft, and a plug-in stop block and a limiting stop block located at a lower end of the plug-in stop block are formed on an outer surface of the spring contact strip, where upper and lower end surfaces of the plug-in stop block and a lower end surface of the limiting stop block are inclined guide surfaces, and an upper end surface of the limiting stop block is of a vertical surface structure.

Further, the adjustment gear is of a bevel gear structure, and correspondingly, the gear rings that are of the compound gear and that are engaged with the adjustment gear are of a worm transmission structure.

Further, an arc-shaped travel limiting slot is formed on the articulated connection arm on one side of the gearbox housing, and a travel distance of the travel limiting slot corresponds to an angle-adjustable travel of the correction bracket; and a limiting post that is embedded into the travel limiting slot is formed on a side end surface of the pivot shaft.

Further, non-slip patterns are disposed in a circumferential direction of the adjustment knob; and/or a gearbox housing configured to mount the rotational adjustment mechanism is disposed on the fastening bracket, and the gearbox housing is longitudinally rotatable relative to the fastening bracket.

Further, a detachable buffer pad is disposed on an inner side of the fastening bracket.

Further, the detachable connection manner includes one of snap-fit, a hook-and-loop fastener, and magnetic attraction, and the buffer pad includes one of a silicone pad and a foam pad.

The present disclosure has the following beneficial effects: A rotational adjustment mechanism can be disposed to rotationally adjust a lateral angle of a correction bracket, effectively resolving problems such as cumbersome use and operation, limited angle adjustment, and poor correction effect of a current orthotic device on the market. In addition, a gear adjustment structure is adopted, achieving stable and efficient overall adjustment. The high structural strength of the overall structure provides exceptional stability during use, thereby effectively avoiding an angle loss.

DETAILED DESCRIPTION OF THE EMBODIMENTS

Figure 1:
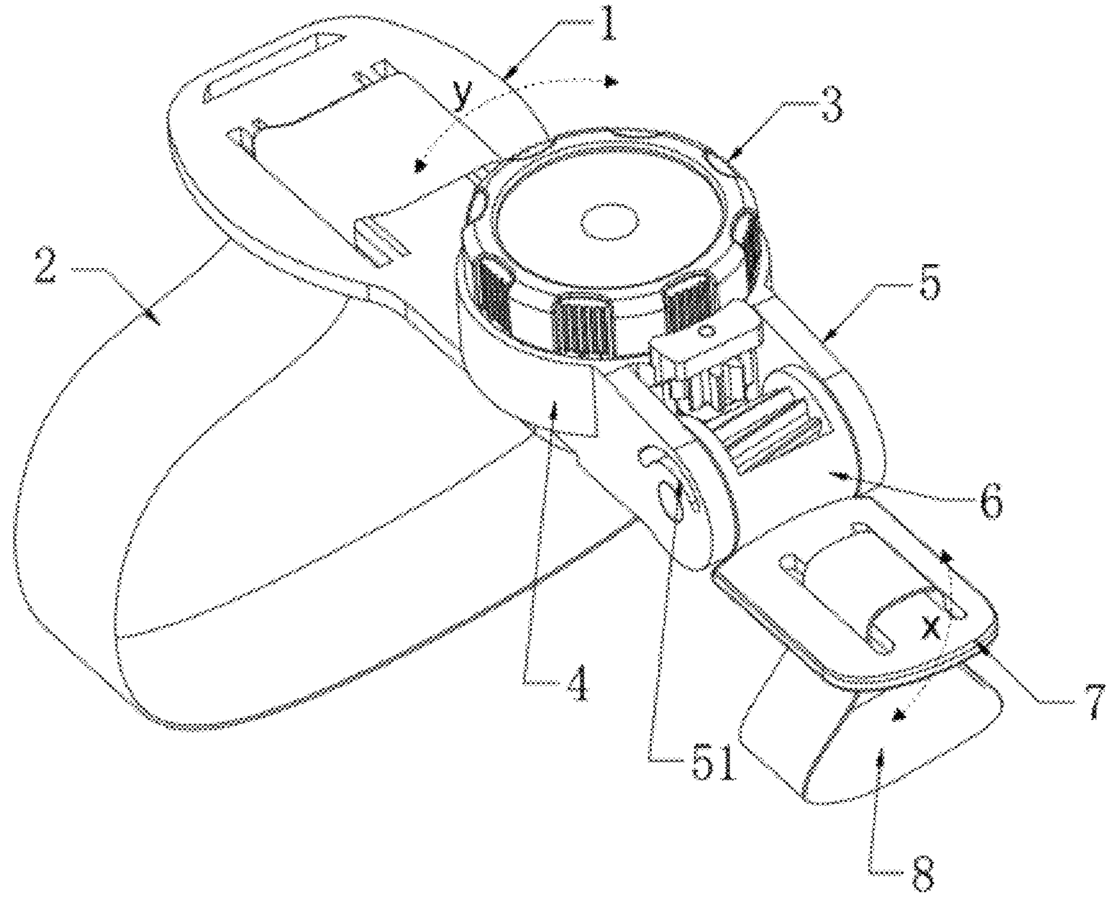
FIG. 1 is a schematic structural diagram according to the present disclosure.
Figure 2:
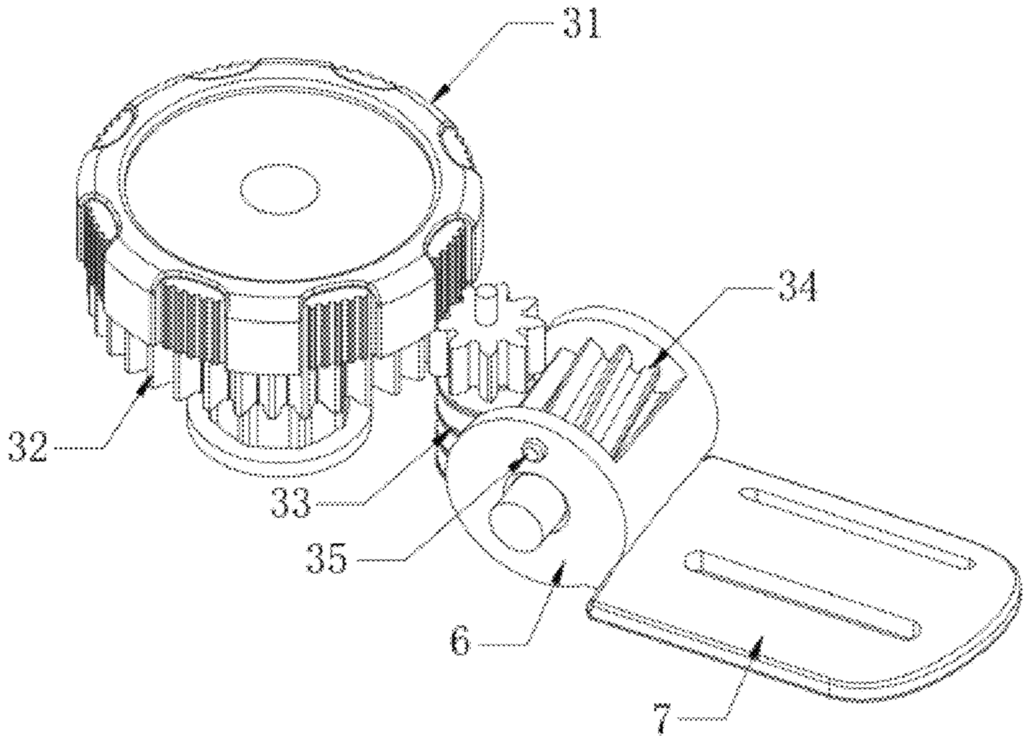
FIG. 2 is a schematic structural diagram of a rotational adjustment mechanism according to the present disclosure.
Figure 3:
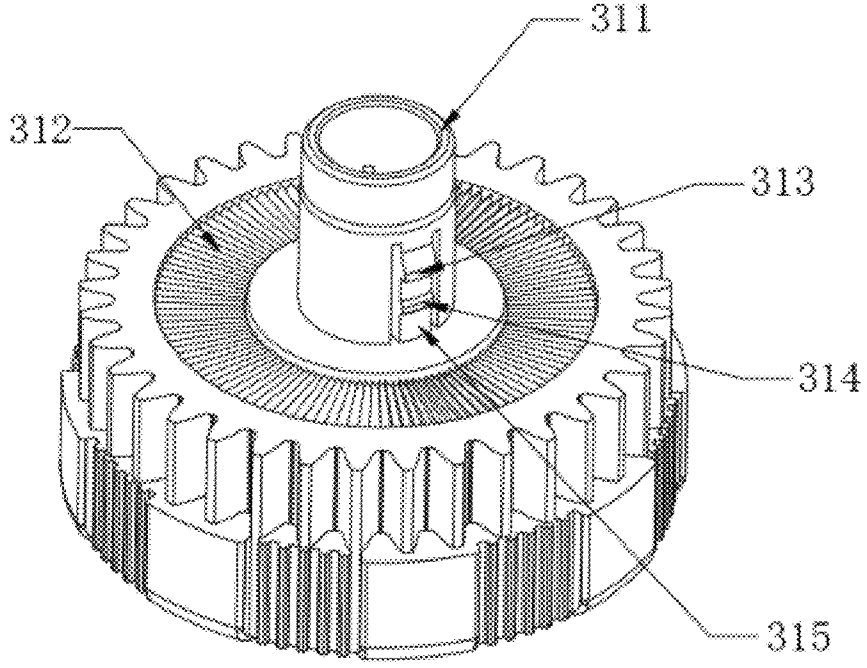
FIG. 3 is a schematic structural diagram of an adjustment knob according to the present disclosure.
Figure 4:
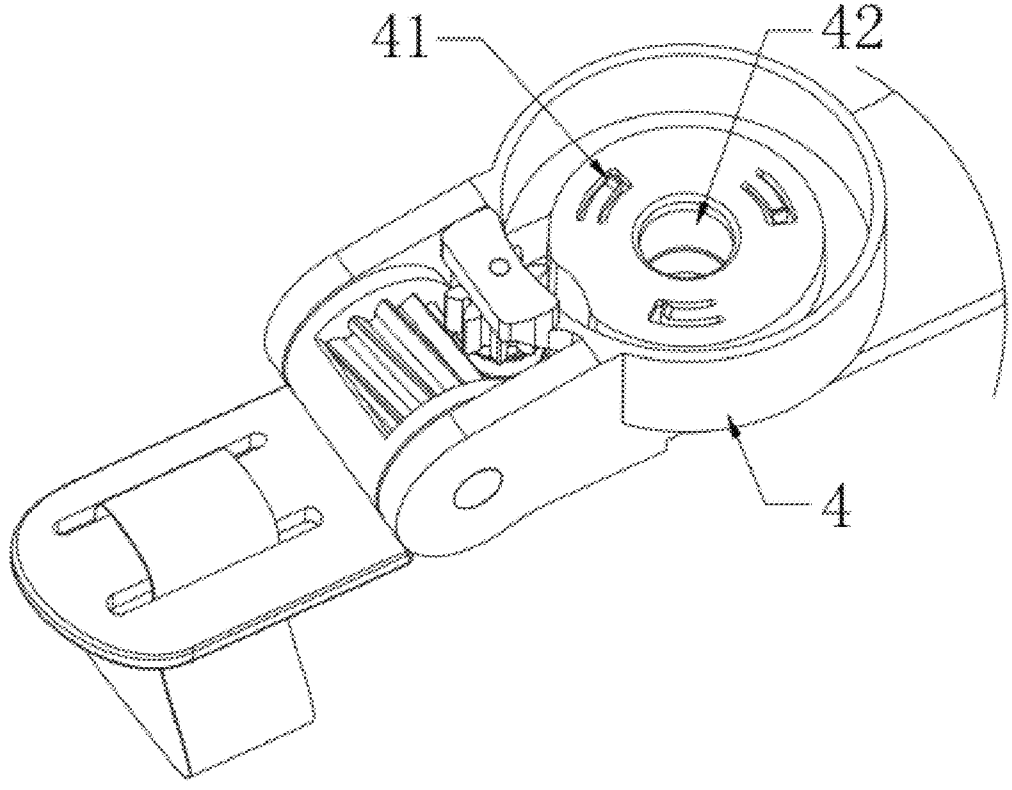
FIG. 4 is a schematic structural diagram of a gearbox housing according to the present disclosure.
Figure 5:
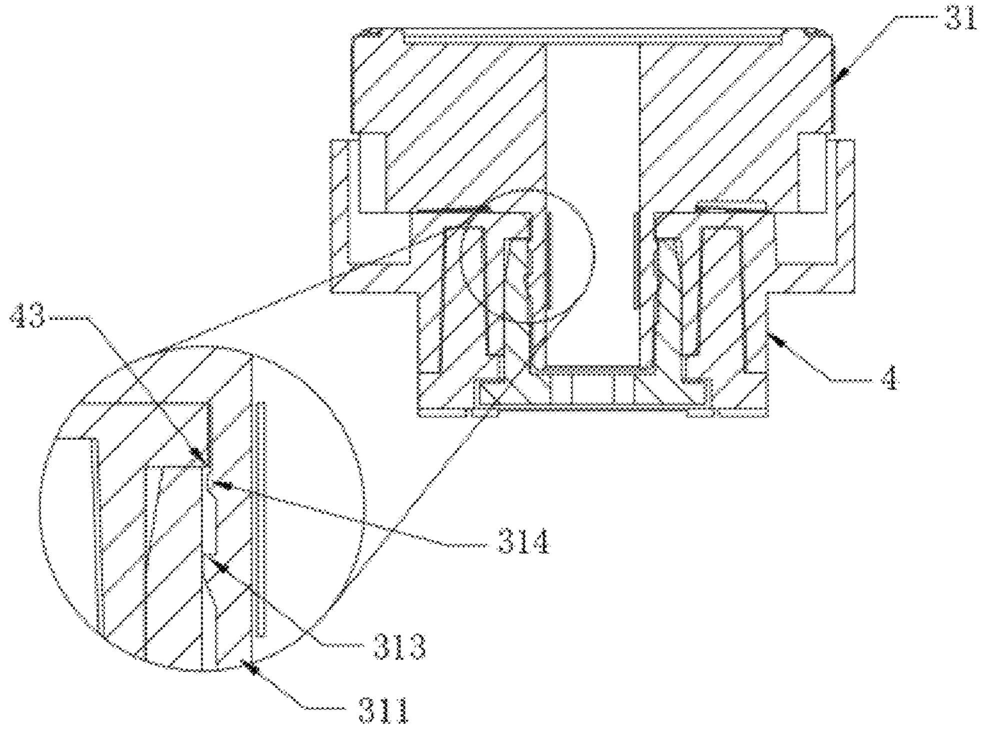
FIG. 5 is a schematic structural diagram of an adjustment knob according to the present disclosure.

The technical solutions in the embodiments of this application are clearly and completely described below with reference to the drawings in the embodiments of this application. Apparently, the described embodiments are only some rather than all of the embodiments of this application. It should be understood that the present application is not limited by the examples and embodiments publicly described herein. All other embodiments obtained by a person of ordinary skill in the art based on the embodiments of the present application without creative efforts shall fall within the protection scope of the present application.

In the description of the present disclosure, it should be understood that orientations or position relationships indicated by terms "length", "width", "upper", "lower", "front", "rear", "left", "right", "vertical", "horizontal", "top", "bottom", "inside", "outside", and the like are orientations or position relationships as shown in the drawings, for ease of describing the present disclosure and simplifying the description, rather than indicating or implying that the mentioned devices or elements must have a specific orientation and must be established and operated in a specific orientation, and thus, these terms cannot be understood as a limitation to the present disclosure.

In addition, the terms "first" and "second" are merely intended for a purpose of description, and shall not be understood as an indication or implication of relative importance or implicit indication of a quantity of indicated technical features. Thus, features defined with "first" and "second" may explicitly or implicitly include one or more of the features. In the description of the present disclosure, the term "a plurality of" means two or more, unless otherwise specifically defined.

In the present disclosure, unless otherwise clearly specified, the terms "installation", "interconnection", "connection" and "fixation" are intended to be understood in a broad sense. For example, the connection may be a fixed connection, removable connection or integral connection; may be a mechanical connection or electrical connection; may be a direct connection or indirect connection using a medium; and may be a communication or interaction between two elements. Those of ordinary skill in the art may understand the specific meanings of the above terms in the present disclosure based on specific situations.

Refer to FIG. 1 to FIG. 6. In embodiments of the present disclosure, a novel toe corrector includes a fastening bracket 1 that extends longitudinally, a correction bracket 7 that extends longitudinally, and a rotational adjustment mechanism 3 configured to adjust the correction bracket 7.

An adjustable fastening strap 2 that is configured to fasten the fastening bracket 1 to a medial side of a foot is disposed on the fastening bracket 1.

An adjustable correction strap 8 that is configured to fasten the correction bracket 7 to the medial side of the foot is disposed on the correction bracket 7.

The rotational adjustment mechanism 3 includes an adjustment knob 31 that is disposed on the fastening bracket 1 and an adjustment gear 34 that is in meshing engagement with the adjustment knob. A drive gear 32 that is coaxial with the adjustment knob 31 is disposed at a lower end of the adjustment knob 31, and the drive gear 32 is in meshing engagement with the adjustment gear 34. The adjustment gear 34 is connected to the correction bracket 7. The adjustment knob 31 and the adjustment gear 34 are constructed to enable the fastening bracket 1 to be in articulated joint with the correction bracket 7. The correction bracket 7 is horizontally rotatable relative to the fastening bracket 1.

The fastening bracket 1 is in articulated joint with the correction bracket 7. The rotational adjustment mechanism 3 is disposed on an articulated position. The correction bracket 7 is driven by the rotational adjustment mechanism 3 to implement horizontal rotation, namely, rotation in a horizontal direction, specifically a direction indicated by a line x in FIG. 1 and FIG. 6.

In use, the fastening bracket 1 is fastened to the side of the foot through the adjustable fastening strap 2, and the correction bracket 7 is fastened to the big toe through the adjustable correction strap 8. The correction bracket 7 is driven by the rotational adjustment mechanism 3 to rotate toward the inner side. Specifically, the adjustment knob 31 is operated to rotate, and the drive gear 32 rotates accordingly, thus driving the adjustment gear 34 to drive the correction bracket 7 to rotate. The adjustment knob 31 is operated to respectively rotate in two directions, to drive the correction bracket 7 to turn over inward or outward relative to the fastening bracket 1. Therefore, bunions or inward deviation of the big toe can be corrected to a normal position, achieving the corrective positioning effect of the big toe.

Further, the rotational adjustment mechanism 3 further includes a compound gear 33 that is in meshing engagement between the adjustment knob 31 and the adjustment gear 34. Two gear rings of the compound gear 33 are respectively in meshing engagement with the drive gear 32 and the adjustment gear 34, and are configured to transmit power of the adjustment knob 31 to the adjustment gear 34, achieving angle adjustment of the correction bracket 7. It may be understood that, in another embodiment, the compound gear 33 may be omitted, and the adjustment knob 31 is in directly in transmission connection to the adjustment gear 34.

In use, the adjustment knob 31 can be adjusted to adjust a rotation angle of the correction bracket 7 through the drive gear 32, the compound gear 33, and the adjustment gear 34, to meet different use needs. In addition, the gear adjustment structure has higher overall structural strength, making the corrector have good stability in a use process, and avoiding an angle loss condition.

A gearbox housing 4 configured to mount the rotational adjustment mechanism 3 is disposed on the fastening bracket 1, to mount the rotational adjustment mechanism 3 and achieve articulated joint between the fastening bracket 1 and the correction bracket 7.

Two articulated connection arms 5 extending toward the correction bracket 7 are respectively formed on two sides of the gearbox housing 4. A pivot shaft 6 is disposed at an end of the correction bracket 7, the pivot shaft is received between two groups of articulated connection arms 5, and is in articulated joint with the two groups of articulated connection arms 5. The adjustment gear 34 is disposed in the pivot shaft 6 and is coaxial with the pivot shaft 6.

Further, the adjustment knob 31 is axially movably engaged with the gearbox housing 4, and ratchets 312 that are circumferentially disposed are formed on a lower end surface of the drive gear 32.

Pawls 41 that correspond to the ratchets 312 are disposed at a bottom of the gearbox housing 4, and the ratchets 312 are engaged with the pawls 41 to form a ratchet mechanism.

When the adjustment knob 31 is pressed down, the ratchet 312 is engaged with the pawl 41, so that the adjustment knob 31 performs rotational adjustment in a single direction (an adjustment direction), thereby avoiding an angle loss condition when or after the correction bracket is adjusted. After the adjustment knob 31 is pulled up, the ratchet 312 is separated from the pawl 41, achieving adjustment for positive and negative angles.

To implement that the adjustment knob 31 is movable and pluggable in an axial direction in the gearbox housing 4, a central shaft 311 extending downward is formed at a lower end of the adjustment knob 31. A mounting shaft hole 42 for allowing the central shaft 311 to insert is provided in the gearbox housing 4. A limiting flange 43 extending inward is formed on an upper edge of the mounting shaft hole 42.

A spring contact strip 315 that is elastically connected to the central shaft 311 is formed on the central shaft 311. A plug-in stop block 314 and a limiting stop block 313 located at a lower end of the plug-in stop block 314 are formed on an outer surface of the spring contact strip 315.

Upper and lower end surfaces of the plug-in stop block 314 and the lower end surface of the limiting stop block 313 are inclined guide surfaces. When the adjustment knob 31 is inserted or removed or mounted, the inclined guide surface is configured to insert and remove a guide wire. Through strong deformation, the spring contact strip 315 is pressed into the central shaft 311, smoothly achieving insertion and removal or mounting work of the adjustment knob 31.

Insertion and removal work of the adjustment knob 31 can be achieved through this structural design. In addition, in a non-stress state, the plug-in stop block 314 is pressed against the limiting flange 43, preventing the adjustment knob 31 from unnecessary axial movement.

The upper end surface of the limiting stop block 313 is of a vertical surface structure, avoiding a case of detaching from the gearbox housing 4 during insertion and removal of the adjustment knob.

Further, the adjustment gear 34 is of a bevel gear structure, and gear rings that are of the compound gear 33 and that are engaged with the adjustment gear 34 are of a worm transmission structure with technical features of a large speed, self-locking performance, and a stable structure. An increase in an adjustment gear ratio of the rotational adjustment mechanism 3 can provide a higher correction force, and also maintain the effect of precise adjustment.

Further, an arc-shaped travel limiting slot 51 is formed on the articulated connection arm 5 on one side of the gearbox housing 4, and a travel distance of the travel limiting slot 51 corresponds to an angle-adjustable travel of the correction bracket 7.

A limiting post 35 that is embedded into the travel limiting slot 51 is formed on a side end surface of the pivot shaft 6. During adjustment, the limiting post 35 fits the travel limiting slot 51, to achieve adjustment and limitation of the correction bracket 7, avoiding an over-travel condition.

Further, non-slip patterns 311 are disposed in a circumferential direction of the adjustment knob 31, to avoid slip during a touch operation of a user. The non-slip patterns 311 may be continuous, or may be spaced apart.

Figure 6:
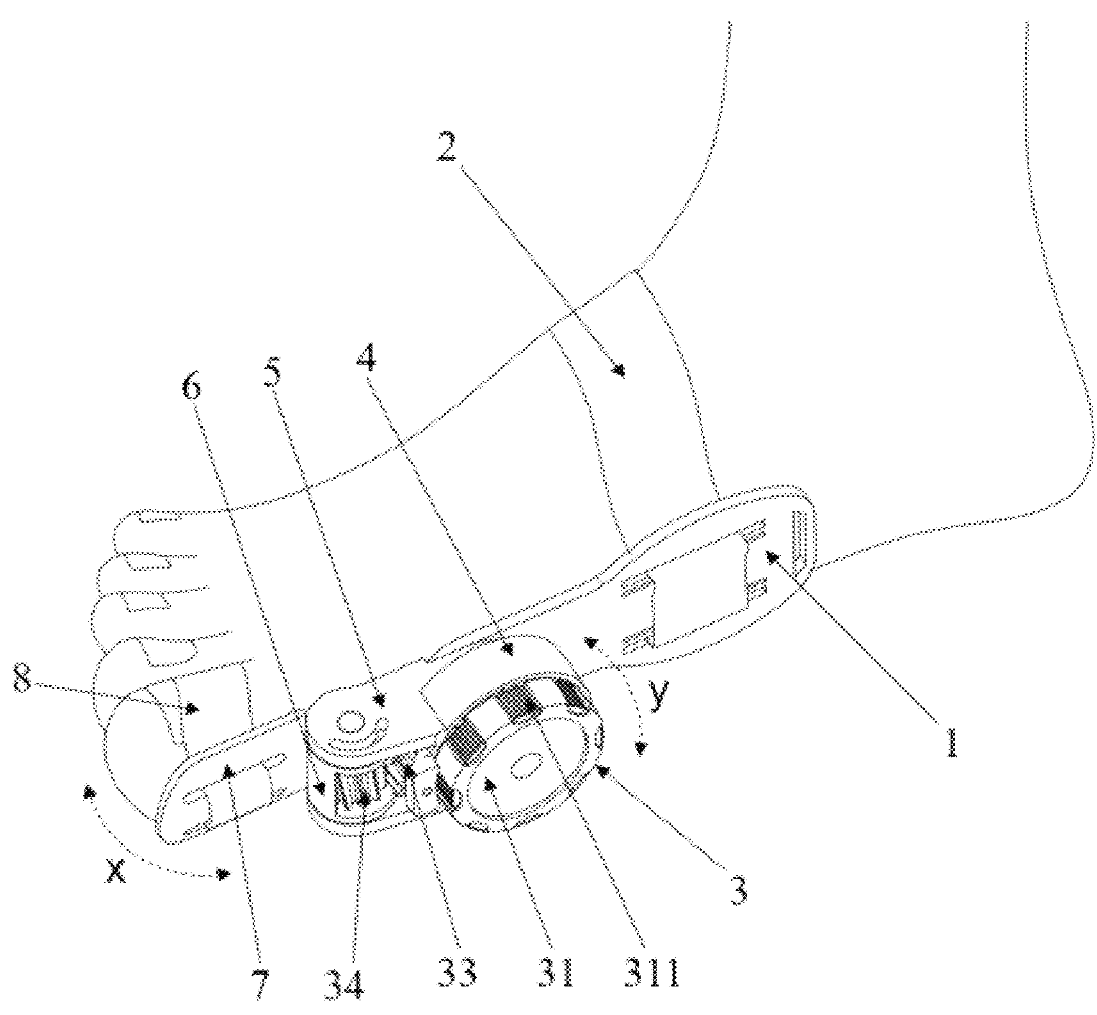
FIG. 6 is a schematic diagram of a use state maker according to the present disclosure.

Further, a gearbox housing 4 configured to mount the rotational adjustment mechanism 3 is disposed on the fastening bracket 1, and the gearbox housing 4 is longitudinally rotatable relative to the fastening bracket 1, that is, rotatable in a horizontal direction, specifically a direction indicated by a line x in FIG. 1 and FIG. 6. Specifically, connection between the fastening bracket 1 and the gearbox housing 4 provides a specific amount of damping, so that the gearbox housing 4 cannot rotate freely up and down relative to the fastening bracket 1, to maintain a stable correcting posture.

Further, a detachable buffer pad (not shown in the figure) is disposed on an inner side of the fastening bracket 1, and is configured to be in buffer contact with the foot.

Further, the detachable connection manner includes one of snap-fit, a hook-and-loop fastener, and magnetic attraction, and the buffer pad includes one of a silicone pad and a foam pad.

It should be further noted that, in this description, relationship terms such as first and second are only used to distinguish an entity or operation from another entity or operation, but do not necessarily require or imply that there is any actual relationship or order between these entities or operations. In addition, terms “include”, “comprise”, or their any other variations are intended to cover a non-exclusive inclusion, so that a process, a method, an article, or a device including a series of elements not only includes those elements, but also includes other elements that are not explicitly listed, or also includes inherent elements of the process, the method, the article, or the device. In the case that there are no more restrictions, an element limited by the statement “includes a . . . ” does not exclude the presence of additional identical elements in the process, the method, the article, or the device that includes the element.

The above description of the disclosed embodiments can enable a person skilled in the art to implement or practice this application. Various modifications to the embodiments are readily apparent to a person skilled in the art, and the generic principles defined herein may be practiced in other embodiments without departing from the spirit or scope of this application. Thus, this application is not limited to the embodiments shown herein but falls within the widest scope consistent with the principles and novel features disclosed herein.

What is claimed is:

1. A toe corrector, comprising: a fastening bracket that extends longitudinally, a correction bracket that extends longitudinally, and a rotational adjustment mechanism configured to adjust the correction bracket, wherein an adjustable fastening strap that is configured to fasten the fastening bracket to a medial side of a foot is disposed on the fastening bracket;

an adjustable correction strap that is configured to fasten the correction bracket to the medial side of the foot is disposed on the correction bracket; and the rotational adjustment mechanism comprises an adjustment knob that is disposed on the fastening bracket and an adjustment gear, wherein a drive gear that is coaxial with the adjustment knob is disposed at a lower end of the adjustment knob, the drive gear is in meshing engagement with the adjustment gear, the adjustment gear is connected to the correction bracket, the adjustment knob and the adjustment gear are constructed to enable the fastening bracket to be articulated with the correction bracket, and the correction bracket is horizontally rotatable relative to the fastening bracket;

wherein the rotational adjustment mechanism further comprises a compound gear that is in meshing engagement between the adjustment knob and the adjustment gear, and two gear rings of the compound gear are respectively in meshing engagement with the drive gear and the adjustment gear.

2. The toe corrector according to claim 1, wherein a gearbox housing configured to mount the rotational adjustment mechanism is disposed on the fastening bracket; and two articulated connection arms extending toward the correction bracket are respectively formed on two sides of the gearbox housing, a pivot shaft is disposed at an end of the correction bracket, the pivot shaft is received between the two articulated connection arms, and is articulated with the two articulated connection arms, and the adjustment gear is disposed in the pivot shaft and is coaxial with the pivot shaft.

3. The toe corrector according to claim 2, wherein the adjustment knob is axially movably engaged with the gearbox housing, and ratchets that are circumferentially disposed are formed on a lower end surface of the drive gear; and pawls that correspond to the ratchets are disposed at a bottom of the gearbox housing, and the ratchets are engaged with the pawls to form a ratchet mechanism.

4. The toe corrector according to claim 3, wherein the adjustment knob is configured to be movable and pluggable in an axial direction in the gearbox housing; a central shaft extending downward is formed at a lower end of the adjustment knob; a mounting shaft hole for allowing the central shaft to insert is provided in the gearbox housing; and a limiting flange extending inward is formed on an upper edge of the mounting shaft hole; and a spring contact strip that is elastically connected to the central shaft is formed on the central shaft, and a plug-in stop block and a limiting stop block located at a lower end of the plug-in stop block are formed on an outer surface of the spring contact strip, wherein upper and lower end surfaces of the plug-in stop block and a lower end surface of the limiting stop block are inclined guide surfaces, and an upper end surface of the limiting stop block is of a vertical surface structure.

5. The toe corrector according to claim 2, wherein an arc-shaped travel limiting slot is formed on the articulated connection arm on one side of the gearbox housing, and a travel distance of the travel limiting slot corresponds to an angle-adjustable travel of the correction bracket; and a limiting post that is embedded into the travel limiting slot is formed on a side end surface of the pivot shaft.

6. The toe corrector according to claim 1, wherein the adjustment gear is of a bevel gear structure, and correspondingly, the gear rings that are of the compound gear and that are engaged with the adjustment gear are of a worm transmission structure.

7. The toe corrector according to claim 1, wherein non-slip patterns are disposed in a circumferential direction of the adjustment knob; and/or a gearbox housing configured to mount the rotational adjustment mechanism is disposed on the fastening bracket, and the gearbox housing is longitudinally rotatable relative to the fastening bracket.

* * * * *